United States Patent
Uustare et al.

(10) Patent No.: US 10,668,166 B2
(45) Date of Patent: Jun. 2, 2020

(54) ANTIBODY-DRUG-CONJUGATES COMPRISING NOVEL ANTHRACYCLINE-DERIVATIVES FOR CANCER TREATMENT

(71) Applicant: Toxinvent Oü, Tartu (EE)

(72) Inventors: Ain Uustare, Tartu (EE); Ivan Ogibalov, Tartu (EE); Olga Tšubrik, Tartu (EE); Andrus Tasa, Tartu (EE); Uno Mäeorg, Tartu (EE); Ago Rinken, Tartu (EE)

(73) Assignee: Toxinvent Ou, Tartu (EE)

( * ) Notice: Subject to any disclaimer, the term of this patent is extended or adjusted under 35 U.S.C. 154(b) by 0 days.

(21) Appl. No.: 16/303,861

(22) PCT Filed: May 30, 2017

(86) PCT No.: PCT/EP2017/062989
§ 371 (c)(1),
(2) Date: Nov. 21, 2018

(87) PCT Pub. No.: WO2017/207540
PCT Pub. Date: Dec. 7, 2017

(65) Prior Publication Data
US 2019/0262464 A1   Aug. 29, 2019

(30) Foreign Application Priority Data
May 30, 2016   (GB) .................................. 1609464.1
Mar. 3, 2017   (GB) .................................. 1703503.1

(51) Int. Cl.
| C07D 498/04 | (2006.01) |
| A61K 47/68  | (2017.01) |
| A61K 31/424 | (2006.01) |
| C07H 15/252 | (2006.01) |

(52) U.S. Cl.
CPC ........ *A61K 47/6809* (2017.08); *A61K 31/424* (2013.01); *C07D 498/04* (2013.01); *C07H 15/252* (2013.01)

(58) Field of Classification Search
CPC .................................................. C07D 498/04
See application file for complete search history.

(56) References Cited

U.S. PATENT DOCUMENTS

4,673,668 A * 6/1987 Ishizumi .............. C07H 15/252
                                              514/34
5,877,296 A     3/1999 Hamann et al.
7,276,497 B2  10/2007 Chari et al.
7,659,241 B2   2/2010 Senter et al.

FOREIGN PATENT DOCUMENTS

| EP | 0107486 A1 | 5/1984 |
| EP | 2303332 B1 | 12/2014 |
| EP | 2948183 B1 | 4/2016 |
| GB | 201609464 | 5/2016 |
| GB | 201703503 | 3/2017 |
| WO | WO-2004/067038 A1 | 8/2004 |
| WO | WO-2007/102888 A2 | 9/2007 |
| WO | WO-2015/095223 A2 | 6/2015 |
| WO | WO-2016/071418 A1 | 5/2016 |
| WO | PCT/EP2017/062989 | 5/2017 |

OTHER PUBLICATIONS

Barthel, B.L. et al., Synthesis and Biological Characterization of Protease-Activated Prodrugs of Doxazolidine. J Med Chem. 2012; 55(14):6595-607 (31 pages).
CAS abstract Accession No. 1988:22206 (27 pages), 1988.
Fenick, D.J. et al., Doxoform and Daunoform. Anthracyclin-Formaldehyde Conjugates Toxic to Resistant Tumor Cells. J Med Chem. 1997; 40(16):2452-61.
Ishizumi et al., Stereospecific Total Synthesis of 9-Aminoanthracyclines: (+)-9amino-9-deoxydaunomycin and Related Compounds. J Org Chem. 1987; 52(20):4477-85.
Jeffrey, S.C. et al., Dipeptide-based Highly Potent Doxorubicin Antibody Conjugates. Bioorg Med Chem Lett. 2006; 16(2):358-62.
Search and Examination Report dated Mar. 6, 2017 by the Intellectual Property Office of Great Britain for Patent Application No. GB1609464.1, which was filed on May 30, 2016 and published as GB201609464 D0 dated Jul. 31, 2016 (Inventor—Uustare et al.; Applicant—Toxinvent Oü) (8 pages).
International Search Report and Written Opinion dated Aug. 31, 2017 by the International Searching Authority for Patent Application No. PCT/EP2017/062989, which was filed on May 30, 2017 and published as WO 2017/207540 dated Dec. 7, 2017 (Inventor—Uustare et al.; Applicant—Toxivent Oü) (13 pages).
International Preliminary Report on Patentability dated Dec. 4, 2018 by the International Searching Authority for Patent Application No. PCT/EP2017/062989, which was filed on May 30, 2017 and published as WO 2017/207540 dated Dec. 7, 2017 (Inventor—Uustare et al.; Applicant—Toxivent Oü) (9 pages).

\* cited by examiner

*Primary Examiner* — Matthew P Coughlin
(74) *Attorney, Agent, or Firm* — Ballard Spahr LLP (57) ABSTRACT

The present invention relates to novel anthracycline derivatives comprising two oxazolidine cycles and the preparation of said anthracycline derivatives. Furthermore, antibody-drug conjugates (ADCs) comprising the novel anthracycline derivatives and the use of such ADCs in the prevention and treatment of cancer are disclosed.

14 Claims, 4 Drawing Sheets

ANTIBODY-DRUG-CONJUGATES COMPRISING NOVEL ANTHRACYCLINE-DERIVATIVES FOR CANCER TREATMENT

CROSS-REFERENCE TO RELATED APPLICATIONS

This application is a U.S. National Phase Application of International Application No. PCT/EP2017/062989, filed May 30, 2017, which claims priority to GB Application No. 1609464.1, filed May 30, 2016 and GB Application No. 1703503.1, filed Mar. 3, 2017.

FIELD OF THE INVENTION

The present invention relates to novel anthracycline derivatives comprising two oxazolidine cycles and the preparation of such anthracycline derivatives. Furthermore, antibody-drug conjugates (ADCs) comprising the novel anthracycline derivatives and the use of such ADCs in the prevention and treatment of cancer are disclosed.

BACKGROUND

In the last decades a new class of highly potent biopharmaceutical drugs evolved. Antibody-Drug Conjugates (ADCs) or immune-conjugates are a new class of highly potent biopharmaceutical drugs. They are developed for the targeted cancer therapy and during the last decades they have received the utmost attention in the oncology field.

An ADC is a hybrid of two different worlds. On the one hand the conjugate consists of a monoclonal antibody targeting a tumor-specific antigen. To this biopharmaceutical antibody a highly potent small molecule, i.e. a cytotoxic agent is conjugated (sometimes also called payload or toxin). The monoclonal antibody and the small molecule are conjugated by covalent bonds via a linker fragment that allows chemical conjugation of the toxin molecule to the antibody. This fragment is (optionally) cleaved in target cells and the active toxin is released. Sometimes, a spacer, which may be another small molecule, is also used to increase the distance between antibody and a cytotoxic agent.

The main objective of ADC design and use is to combine the high cytotoxic potency of a small molecule and the high specificity of monoclonal antibody (mAb) for tumor-associated antigen targets. As the toxin is covalently bound to antibody and can be freed only after internalization in the cancer cell, the systemic toxicity is minimized. Due to its highly targeted tumor antigen recognition based on the antibody such conjugate allows excellent discrimination between healthy and cancer cells. In addition, based on the requirement of antigen binding for effective internalization and processing in cells, ADC drugs are expected to provide a wider therapeutic window compared to the cytotoxic agent alone.

Cytotoxic agents used as drug components for ADCs usually comprise 100 to 1000 times higher cytotoxic activity compared to conventionally applied chemotherapy drugs. Different classes of cytotoxic agents have been used for developing of ADCs. The use of Calicheamicins is for instance disclosed in U.S. Pat. No. 5,877,296 A. Maytansinoids are described in U.S. Pat. No. 7,276,497 B2, Monomethylauristatins in U.S. Pat. No. 7,659,241 B2 and Duocarmycins for instance in EP 2 948 183 B1.

The cytotoxic effect of anthracyclines is based on mechanism of action including:

1) intercalation of the anthracycline moiety into the DNA of the cell;

2) production of free radicals which react with DNA and other cellular macromolecules to cause damage to cell components or 3) interactions of the anthracycline drug molecules with the cell membrane.

The free radicals formed by reduction of the anthracycline can oxidize other molecules in the cell to produce formaldehyde, which in turn also reacts with DNA and amino group(s) present in anthracycline, forming covalently linked complex between anthracycline and DNA.

Some anthracyclines like for instance Doxorubicin or Daunorubicin have been widely used in the treatment of numerous cancers such as lung carcinoma, small cell lung cancer, leukemia, breast carcinoma, ovarian adenocarcinoma, different sarcomas and lymphomas, mesothelioma etc. Although anthracyclines belong to the most conventional chemotherapy drugs, most of well-known anthracyclines cannot be used as cytotoxic agents for ADCs. The reason is that the cytotoxic potency of the most common anthracyclines is too low to use them as ADC payload.

Therefore, it is the task of the present invention to provide a new class of anthracyclines comprising higher toxicity compared to state of the art anthracyclines and to provide a reliable route of synthesis to obtain such anthracyclines.

BRIEF DESCRIPTION OF THE INVENTION

Above mentioned problem is solved by a process for production of 9-amino-anthracycline-derivatives at least comprising two oxazolidine moieties at the anthracycline, at least comprising the steps of:

a) Suspending 9-amino-anthracycline according to the following Formula 1 in an aprotic solvent Formula 1 wherein $R^1$ is selected from the group consisting of H, OH, OMe or F and $R^2$ is selected from the group consisting of methyl, ethyl or propyl;

b) Reacting formaldehyde and the two 1,2-amino-alcohol-moieties of the 9-amino-anthracycline to form an anthracycline according to the following Formula 2 comprising two oxazolidine moieties Formula 2

Surprisingly it has been found that it is possible by above described process to synthesize reliably anthracyclines comprising two oxazolidine cycles. Both cycles are synthesized by conversion of 1,2 amino-alcohol-structures of the anthracycline. One of the structures is generated at the sugar moiety and the other oxazolidine cycle is generated by incorporation of the amino group in 9 position of the anthracycline. This reaction drastically increases the cytotoxic potential of the compound, wherein the incorporation of two oxazolidine cycles yields even higher cytotoxicity compared to only 1 cycle analogous. In addition, it is very surprising that especially the 9-amino-anthracyclines are capable of forming such structures, because for other anthracyclines comprising only one 1,2-amino-alcohol-structure at the sugar-moiety it is known that additional formaldehyde results in formation of anthracycline dimers or even higher homologues. Here it is surprising that especially also the sterically hindered 1,2 amino-alcohol-structure at the C9 position is converted without any significant contribution to dimer formation between different anthracyclines. Furthermore, it is surprising that both oxazolidine cycles are generated with the same preference as it is demonstrated by NMR-measurements and that there is no cross reaction between both 1,2 amino-alcohol-structures. This means that by this process a chemically well-defined cytotoxic agent is obtainable which is very potent and suitable for being used in pharmaceutical compositions.

9-amino-anthracycline-derivatives in the sense of this invention are anthracycline molecules comprising two 1,2-amino-alcohol fragments (analogous to L-daunosamine and amrubicinol). Such anthracycline is for instance represented by the following structure (including the C-numbering):

The above displayed structure can be used as an educt for the synthesis of 9-amino-anthracyclines comprising two oxazolidine cycles. Nevertheless, it is clear to the skilled artisan that it is possible to use different pre-cursors as starting material, wherein the different pre-cursors are chemically converted to the 1,2 amino-alcohol-structure. For instance it is possible to use anthracyclines, wherein a ketone-group is attached to C9 as overall starting material, followed by reduction of the ketone to the suitable alcohol, respectively. This means that feasible starting materials include anthracyclines comprising only one 1,2-amino-alcohol-structure and a ketone and an amino group attached to the 9 position, wherein the alcohol-moiety is formed in a separate pre-step.

It can be seen from the above displayed structure that anthracyclines may adopt different stereo-chemical conformations. For instance the carbon atom in the position 13 is chiral and can have two configurations (13-S and 13-R), as shown below:

The two stereo-chemical forms of the carbon 13 give rise to corresponding two diastereomers of oxazolidine cycle formed from the hydroxyl group at C13, amino group at C9 and methylene group, i.e.

The 9-aminosubstituted anthracyclines used as educts in the process of the invention can be either in the form of a pure diastereomer or in form of a mixture of diastereomers. Furthermore, it is poss+ible to use the anthracycline educt with a keto-group in 9 position and either reduce this group non-selective, e.g. by using borohydrides, which yields a mixture of diastereomers or chirally selective reagents, wherein the latter results in the formation of a single diastereomer.

Nevertheless, it has been found that the above displayed reaction is independent of changes in stereochemistry. Therefore, all the further reaction schemes in this application are given without a special, defined stereochemistry.

By the inventive reaction two oxazolidine moieties are generated at the anthracycline. The overall reaction can be visualized by the following scheme, wherein the formaldehyde carbon is integrated into the 1,2-amino-alcohol-structure forming a heterocyclic 5-membered ring structure:

Especially under proteolytic conditions, for instance in the presence of water, the ring structure is in equilibrium with the 1,2 amino-alcohol-structure. In order to shift the equilibrium mostly to the cyclic structure it is possible to prevent the back reaction for instance by adding a protection group to the ring-nitrogen.

Within a first reaction step a) the 9-amino-anthracyclines are suspended in an aprotic solvent. This means that the starting anthracycline is brought in contact with a solvent, wherein the educt does not have to be completely dissolved in the solvent. However, it is preferred that a suspension is generated, wherein undissolved anthracycline is still present. Especially the latter may contribute to achieve a reaction product containing two instead of just one oxazolidine cycle at the 9-amino-anthracycline.

The anthracycline is suspended in an aprotic solvent. Suitable solvents can for instance be selected from pharmaceutically acceptable solvents, wherein solvents comprising a lower polarity are preferred. Especially preferred are solvents with a polarity in the range of larger or equal to 15 and smaller or equal to 40 (water=100). Suitable solvents in that range can for instance be chlorobenzene, chloroform, dichloromethane, pyridine or mixtures thereof. It might also be feasible to work with the deuterated solvent, whereas for the ease of reaction non-deuterated solvents are preferred. Without being bound by the theory it is assumed that especially these solvents are suitable to dissolve the right amount of anthracycline and formaldehyde in order to favour the synthesis of two oxazolidine ring structures. A preferred solvent group comprises a polarity in between 20 and 35.

In step b) formaldehyde and the two 1,2 amino-alcohol-moieties are brought to reaction. The reaction can be performed by the addition of formaldehyde to the suspension. This might be achieved by the addition of a suitable formaldehyde source, like for instance paraformaldehyde. It is also possible to add gaseous formaldehyde to the suspension. In order to prevent the back-reaction from the oxazolidine cycles to the 1,2 amino-alcohol it is preferred that the formaldehyde is added in a water free surrounding. Within the reaction the two 1,2-amino-alcohol-structures are transferred to two oxazolidine cycles by the addition of —$CH_2$— groups, respectively.

In the case that anthracyclines are used as educts, wherein the anthracycline comprise amino groups in a protected form, it is also possible to apply conditions for a de-protection prior the first reaction step resulting in the formation of the unprotected 1,2 amino-alcohol-structures.

In a preferred embodiment of the process the molar ratio of formaldehyde to anthracycline (formaldehyde:anthracycline) in step c) can be ≥0.1 and ≤10. Contrary to the expectation of the skilled artisan it has been found useful to limit the relative amount of formaldehyde to a rather low value, although the formation of two oxazolidine cycles shall be achieved per anthracycline. This ratio may further help to prevent dimerization of the anthracyclines, resulting in higher yields of monomeric anthracycline comprising two oxazolidine cycles. If the reaction is performed at ratios lower than 10, preferably lower than 2, it might be helpful to work up the suspension by filtration, in order to remove unreacted anthracycline. Additionally, the reaction may be performed with molar ratios of formaldehyde to anthracycline of ≥0.5 and ≤5 or preferably in the range of ≥0.75 and ≤3.

In another characteristic of the process the concentration of the anthracycline in the solvent can be ≥5 mM and ≤50 mM. Also a relatively low concentration of the anthracycline might help to increase the selectivity of the overall process. Within this anthracycline concentration range it is possible to achieve high conversion rates to the product comprising two oxazolidine cycles. Lower concentrations might be unfavourable, because of the necessary high reaction volumes, which might increase the costs for the following work-up. Furthermore, this concentration range has been found useful for the separation of unreacted educts by filtration, wherein the unreacted educts remain undissolved under these conditions. This is found contrary to the reaction product containing two oxazolidine cycles, which is fully dissolved under these conditions.

Within a further embodiment of the process the formaldehyde can be used in form of paraformaldehyde and the molar ratio of formaldehyde to anthracycline (formaldehyde:anthracycline) can be ≥1.0 and ≤2.0. It has been found useful to drive the overall reaction with a rather low formaldehyde to anthracycline ratio. Even by using non-stoichiometric formaldehyde it is possible to achieve a reasonable conversion, wherein the overall purity of the generated anthracycline comprising two oxazolidine cycles is very high. Especially the amount of unwanted side-products or dimers is reduced, resulting in a chemically well-defined anthracycline. Without being bound by the theory it is assumed that this reaction conditions are able to completely dissolve the generated anthracycline comprising two cycles in the reaction solvent, whereas unreacted anthracycline or anthracyclines just comprising one cycle remain mainly undissolved. Therefore, it is especially possible to separate the targeted product from unwanted by-products by a simple filtration step. Therefore, in combination with paraformaldehyde in particulate form it is possible to obtain rather pure dissolved product, wherein unreacted educts are removable by filtration.

In another preferred embodiment of the process the solvent is HCCl$_3$. Especially the non-deuterated chloroform has been found useful for being the reaction medium. On the one hand chloroform seems to provide the "right" solubility for the two oxazolidine cycle comprising anthracycline and, on the other hand, the use of non-deuterated solvents reduces the risk of H/D-exchange. In consequence, rather high yields are possible in rather short reaction times and by simple filtration it is possible to achieve a suitable product purity.

Within a further aspect of the process it is possible that in an additional step c) the anthracycline according to Formula 2 is reacted with linker molecules L to form a reaction product according to the following formula 3a-c

Formula 3a

Formula 3b

Formula 3c

Preferably L is a cleavable linker, which is a linker hydrolyzed by enzymes inside target cells to free the active toxin. The linker can be bound to the nitrogen atoms of the oxazolidine cycles by a chemical bond undergoing chemical or enzymatic cleavage inside a target cell, for example by an amide or carbamate bond. The linker can be completely cleavable from the nitrogen atom. Examples of suitable linkers are maleimidocaproyl-L-valine-L-citrulline-p-aminobenzoylcarbamate and maleimidocaproyl-L-phenylalanine-L-lysine-p-aminobenzoylcarbamate linker, which undergo enzymatic hydrolysis followed by self-immolative cleavage of p-aminobenzoyl carbamate. Another example of suitable linker is β-glucouronide. In all cases, the linkers contain a structure fragment suitable for conjugation to monoclonal antibodies, for example a maleimido-group, allowing a conjugation of the linker-toxin-conjugate to an antibody using chemical methods compatible with the anthracycline derivatives of the invention.

Within a further aspect of the process the linker L may be maleimidocaproyl-L-valine-L-citrulline-p-aminobenzoyl¬carbamate according to the following structure Especially this linker group is easily attachable also to nitrogen incorporated in ring-structures like the oxazolidine cycles. The latter can for instance be achieved in an activated form of p-nitrophenylcarbonate. In addition, oxazolidine cycles protected by this linker are very resistant to hydrolysis, which in turn increasing the ability of attaching to linker groups to the different oxazolidine cycles of the anthracycline.

In a further characteristic of the process it is possible that in an additional step d) the not linker-protected oxazolidine ring in formula 3a or 3b is hydrolyzed to yield the respective 1,2 amino-alcohol moiety according to the following formula 4a or 4b

Formula 4a

Formula 4b

In cases wherein only one linker-group is needed for attachment of an antibody it might seem favorable to hydrolyze the generated second oxazolidine cycle to the 1,2-amino-alcohol-structure. Such step may also be performed parallel to linker formation. Therefore, it is possible to drive the reaction in a way that by attaching only one linker to the anthracycline, the other oxazolidine cycle is hydrolysed to the 1,2 amino-alcohol-moiety. Based on the presence of formaldehyde in the cell this reaction is reversible and an anthracycline is interacting with the DNA, wherein two oxazolidine cycles are present. By using such procedure it is possible to fine-tune the solubility characteristics and stability of the anthracycline.

In a preferred embodiment of the process, in an additional step e) an antibody can be attached to the linker L of formulae 3a-c or attached to the linker L of formulae 4a-b to form an Antibody-Drug-Conjugate (ADC). Based on the amount of attached linker molecules it is possible to form either one or two bonds to an antibody to build the ADC. The two linker molecules can be the same or different. Thus, it is possible to tailor the release conditions of the drug from the antibody. For instance it is possible two use different linkers comprising different hydrolysable groups. The release of the drug will only appear if the chemical surrounding is able to hydrolyze both linkers. Therefore, it is possible to increase the side-selectivity of the drug release. Two linker comprising the same hydrolysable group may result in a safer application, because even in the event that one linker is hydrolyzed the other linker is still intact. Furthermore, by using two linker-groups it is possible to better control the regio-selectivity of the antibody-drug attachment, because the drug attachment can be driven in a way that an attachment is only possible if both linker-groups found suitable counterparts in vicinity on the antibody. This might optimize the release kinetics of the drug and, in addition, might be helpful to attach the drug only outside antibody binding domains.

Furthermore, anthracycline at least comprising two oxazolidine moieties at the anthracycline core according to the following Formula 2 are within the scope of the invention Formula 2 wherein $R^1$ is selected from the group consisting of H, OH, OMe or F and $R^2$ is selected from the group consisting of methyl, ethyl or propyl. Especially, these anthracycline comprising two oxazolidine cycles are highly potent drug molecules, comprising a higher cytotoxicity potential compared to state of the art anthracyclines. Therefore, this group of compounds is suitable for being used in the context of ADCs, because even at very low concentrations a high efficiency is obtained. With respect to other advantages and properties of these group of anthracyclines comprising two oxazolidine cycles it is explicitly referred to the advantages and properties as discussed in the background of the inventive process.

In a preferred embodiment anthracyclines are within the scope of invention, wherein $R^2$=methyl. Without being bound by the theory it appears that double oxazolidine cycle formation is easier achieved in cases, wherein less bulky alkyl groups are present at the oxazolidine cycle at the 9 position of the anthracycline. This might also help to easy the generation of a second oxazolidine cycle in the cell by reaction with intracellular formaldehyde in order to further increase the cytotoxicity of the drug moiety. In principle it seems possible to tailor the equilibrium (1,2 amino-alcohol-vs. oxazolidine cycle structure) by alteration of the stereochemistry of this group. In consequence it is possible to also tailor the cytotoxicity of the anthracycline by this parameter.

In a further preferred characteristic of the anthracycline the group $R^1$ is H.

Furthermore, it is intended to disclose an intermediate in the production of an Antibody-Drug-Conjugate (ADC) comprising an anthracycline structure according to any of the above displayed formulae 3a-3c or according to any of the formulae 4a-4b. The linker protected anthracyclines either comprising one or two linker protected oxazolidine cycles comprise a higher resistance to hydrolysis and therefore are very storage stable. In addition, as already discussed these drugs and drug-linker-conjugates are highly flexible and can be tailored with respect to attachment and reactivity to different needs.

Also an antibody-drug-conjugate comprising an antibody, one or two linker-groups and a drug, is in the scope of the invention, wherein the drug is a 9-amino-anthracycline and the anthracycline comprises two oxazolidine moieties or one oxazolidine moiety and an 1,2-amino-alcohol-moiety at the anthracycline. Based on the increased toxicity of the drug and the increased flexibility with respect to the linker selection and number of linker connections to the antibody it is possible to especially tailor the properties of ADCs by using this class of compounds.

In addition, also a pharmaceutical composition at least comprising the Antibody-drug-conjugate according to the invention in a pharmaceutical acceptable carrier is within the scope of the invention. The anthracyclines of the invention can be conjugated chemically to monoclonal antibodies using suitable reactive linker groups to form Antibody-Drug conjugates (ADCs). Methods for conjugation of drug-linker complexes to monoclonal antibodies are known to persons skilled in the art. Such ADCs can be used to target and destroy cancer cells, and with that to cure cancer, if an antibody specifically targeting markers of cancer cells is used. Some examples of suitable markers (antigens) are CD30 (Hodgkin's lymphoma), CD33 (Myeloid leukemia), CD22 (B-cell lymphoma), CanAg (Carcinomas), PSCA (Prostate cancer). These markers have been found useful as targets for ADC-s. Suitable carrier materials may either be pharmaceutically acceptable solvents, suitable for dissolving the ADC and followed by enteral, parenteral, intravenous or local application. It may also be suitable to use pharmaceutically acceptable suspensions of the ADC.

Furthermore, it is within the scope of the invention to disclose the use of a pharmaceutical composition comprising the inventive anthracyclines for the treatment of cancer. The treatment or the cure of a cancer patient using a conjugate of the inventive anthracyclines with tumor-targeting monoclonal antibody (ADC) involves administration of the ADC to the patient. The administration may preferably include an injection or infusion of a solution or suspension of the ADC.

BRIEF DESCRIPTION OF THE DRAWINGS

Figure 1:
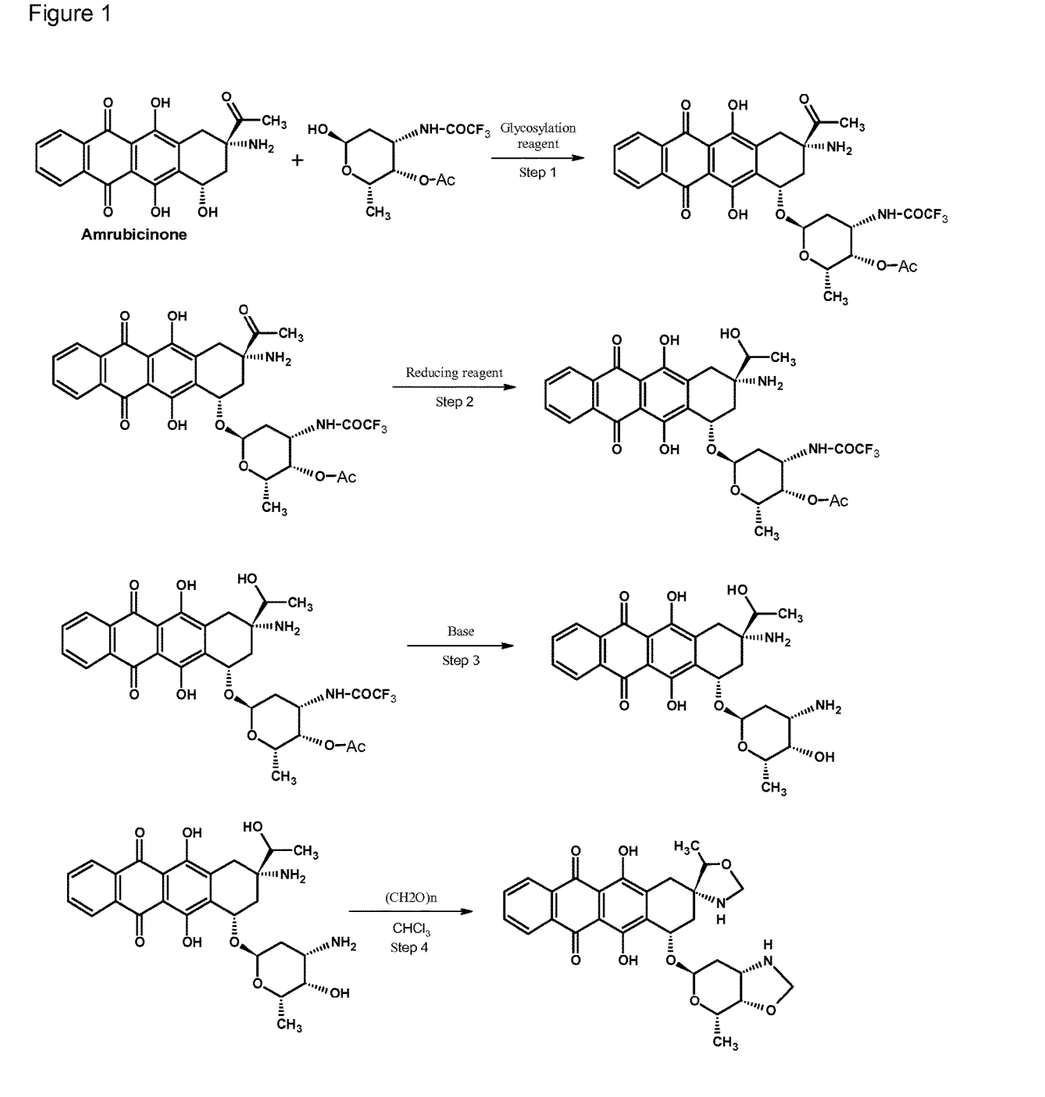
Figure 2:
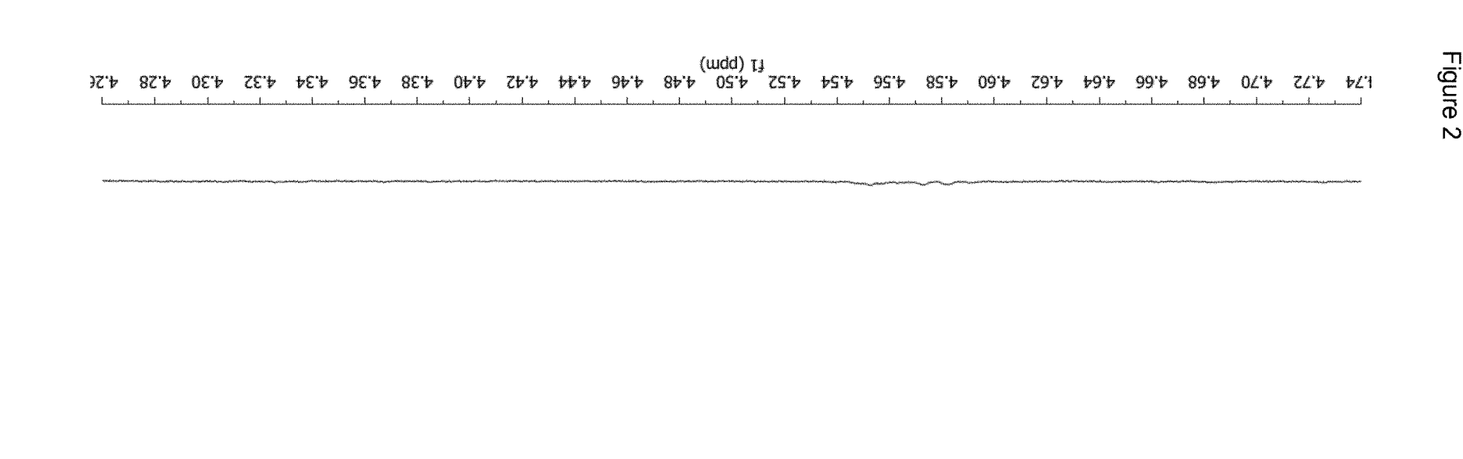
Figure 3:
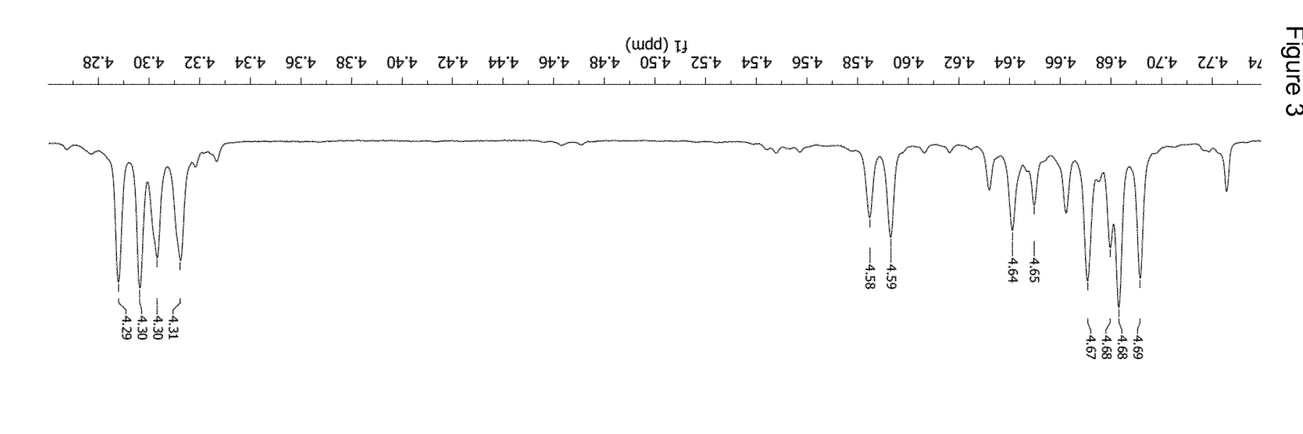
Figure 4:
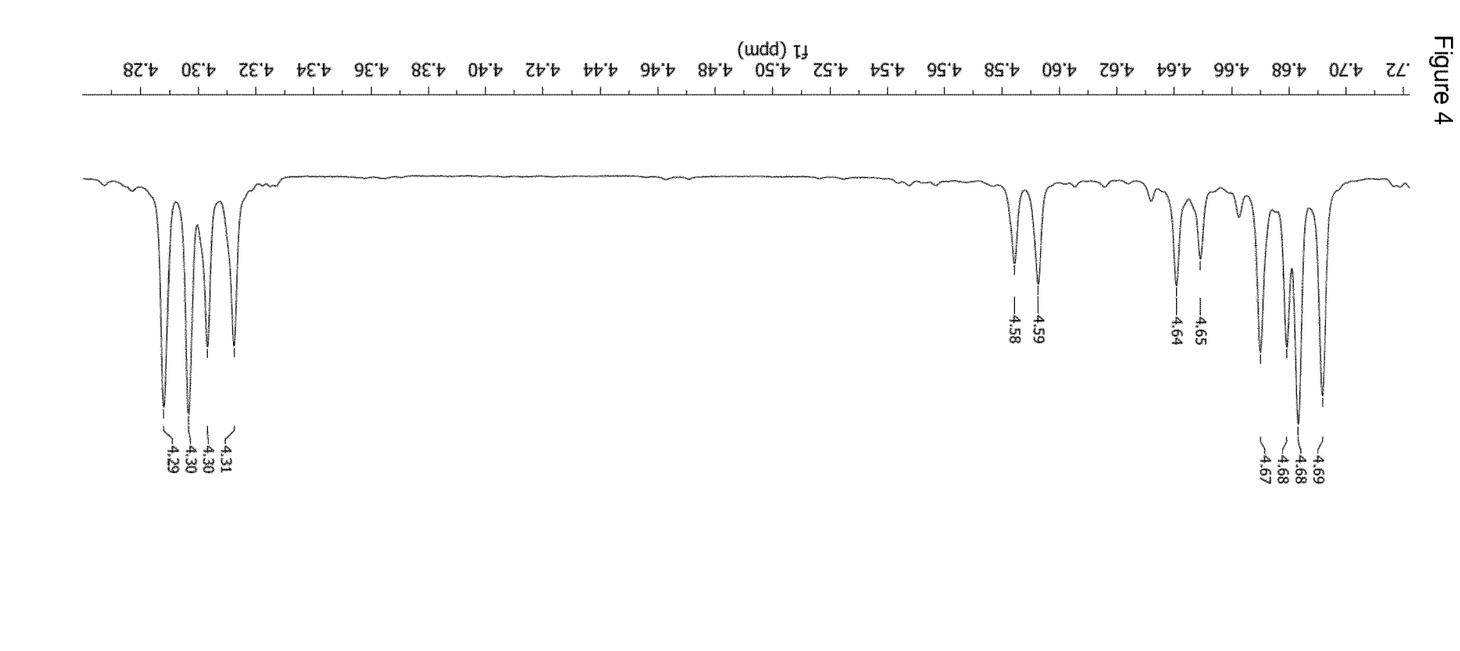

FIGS. 1 to 4 display
FIG. 1 a schematic overview of one inventive route of synthesis
FIG. 2 a $^1$H-NMR of the starting material before reacting the 9-amino-anthracycline with formaldehyde;
FIG. 3 $^1$H-NMR after 24 hours reaction time;
FIG. 4 $^1$H-NMR after 120 hours reaction time.
FIG. 1 is a schematic diagram of a possible route of synthesis. The overall process is displayed using Amrubicinone as starting material. The process starts with a glycosylation in step 1. A sugar is used for the glycosylation, wherein the functional groups of the 1,2 amino-alcohol moiety are protected. In addition in 9-position of the anthracycline a keto-group is present. Consequently, the keto-group is reduced to the respective alcohol in step 2, followed by de-protection of the functional amino-alcohol-moieties in step 3. In step 4 both 1,2 amino-alcohol-moieties are reacted with formaldehyde to yield the anthracycline comprising two oxazolidine cycles. If necessary the modified anthracycline can be reacted with suitable linker groups. In this step either both oxazolidine cycles may be reacted with linker molecules or only one of the oxazolidine cycles. Furthermore, it is possible to hydrolyse one of the oxazolidine cycles to the respective 1,2 amino-alcohol-structure at or prior linking to an antibody.

FIGS. 2-4 shows the $^1$H-NMR spectra in the range of 4.26 up to 4.74 ppm as a function of anthracycline and formaldehyde reaction time (according to the described experimental example, step 4). The signal for the (—CH$_2$—) groups of the oxazolidine cycle appear in this ppm-range. If a bicyclic oxazolidine anthracycline is present it will be present in form of two diastereomers, because the carbon C13 is racemic (the cycle attached to the C9). Consequently, in that case two sets of signals are visible in the NMR spectra. $^1$H-NMR shifts for the (—CH$_2$—) groups generated by oxazolidine cyclisation can be attributed to signals at 4.30/4.69 ppm (two doublets, at the sugar moiety) and at 4.31/4.68; 4.59/4.65 ppm (four doublets, ring at the C9-position), respectively.

FIG. 2 exhibits a $^1$H-NMR spectrum in the range of 4.26 up to 4.74 ppm prior a reaction of the 9-amino-anthracycline with formaldehyde. In the displayed range no signals are visible, indicating that no oxazolidine cycles are present in the educt.

FIG. 3 displays a $^1$H-NMR-spectrum after 24 h reaction time. It is clearly visible that both oxazolidine cycles are formed simultaneously.

FIG. 4 exhibits the $^1$H-NMR-spectrum after 100 h reaction time. Also here it can be deduced from the peak intensities that by the inventive process two oxazolidine cycles are generated.

EXPERIMENTAL EXAMPLES

1. Step—Glycosylation

The starting amrubicinone 100 mg (0.273 mmol) and 1,4-di-O-acetyl-N-trifluoroacetyl-β-L-daunosamine 178 mg (0.545 mmol, 2 eq.) were dissolved in 20 ml dry THF under an argon atmosphere. 4 Å molecular sieves (161 mg) were added, followed by dropwise addition of 25 ml of diethyl ether to the stirred reaction mixture. The reaction mixture was cooled to −33° C.-30° C. and then 119 mg (0.545 mmol, 2 eq.) trimethylsilyl trifluoromethanesulfonate (TMSOTf) was added. After addition of TMSOTf, the reaction mixture was stirred for 1-1.5 h at −33° C.-30° C. and then stirring was continued at −25° C.-20° C. The conversion was monitored by TLC. After the reaction ceased, the reaction mixture was poured under stirring into a pre-cooled (0° C.) mixture of 25 ml saturated NaHCO$_3$ aq. solution and 30 ml of ethyl acetate. The phases were separated and the aqueous phase was extracted once with ethyl acetate (15 ml). The organic phases were combined, washed with brine and dried over Na$_2$SO$_4$. The solvent was evaporated and the crude product was purified by column chromatography on silica gel (eluent: diethyl ether/ethyl acetate). 83 mg (48%) of target compound was obtained.

2. Step—Reduction of the Keto-Moiety

To a solution of 50 mg (0.0788 mmol) of the coupling product from step 1 in 3 ml dry ethanol was added 35 mg (2.1 eq) NaHB(OAc)$_3$. The reaction mixture was stirred for 1 h and the consumption of the starting material was confirmed by TLC monitoring. The solvent was evaporated and 3 ml water was added to the residue. The target product was extracted by diethyl ether (3×10 ml), organic phases were combined, the solvent was evaporated under reduced pressure and the crude product was dried in vacuo. The product was purified by preparative TLC (Eluent DCM/MeOH 19/1) Rf=0.25-0.3. 18 mg (36%) of pure product was obtained.

3. Step—De-Protection

The reduced product prepared according to step 2 (77 mg, 0.121 mmol) was dissolved in 12 ml mixture THF/MeOH/H$_2$O 2/2/1 and then 51 mg (10 eq) of LiOH*H$_2$O was added at 0° C. The reaction mixture was stirred for 15 h at 0° C. After this period, 20 ml water was added to the violet-colored mixture and the mixture was neutralized to pH 8.2-8.3 by dropwise addition of HCl 10%-aq. solution. The target product was extracted by 3*30 ml chloroform. The combined organic extracts were dried over Na$_2$SO$_4$ and the solvent was evaporated under reduced pressure. The crude product was triturated with diethyl ether and the formed precipitate was separated by centrifugation. 20 mg (33%) of pure material was obtained.

4. Step—Ring Formation

-continued 20 mg of de-protected 9 amino anthracycline from step 3 was suspended in 5 ml of dry chloroform. 1.2 mg (1.9 eq.) of solid paraformaldehyde was added and the mixture was stirred for 3 days at room temperature. Paraformaldehyde and unreacted starting material were removed by filtration. The filtrate was concentrated and triturated with diethyl ether. The solid red precipitate was separated, 12.5 mg of product was obtained. The presence of two oxazolidine cycles at the anthracycline was verified by NMR (see FIGS. 2-4). The product had acceptable purity according to NMR spectra and was used without further purification.

5. Step—Linker Attachment 10 mg of the di-oxazolidine product from the previous step was dissolved in 1 ml of dry DMSO, 14 mg (19 µmol, 1 eq.) of maleimidocaproyl-L-valine-L-citrulline-p-aminobenzyl alcohol p-nitrophenyl carbonate (MC-Val-Cit-PABC-PNP), 2.9 mg 1-hydroxybenzotriazole and 6.6 µl of diisopropylethylamine were added to the mixture. The reaction mixture was stirred for 24 h at room temperature. The reaction mixture was poured into 10% solution of citric acid, the red precipitate was separated by filtration and the crude product was purified by preparative HPLC.

6 mg (28%) of the target 9-aminoanthracycline conjugated to MC-Val-Cit-PABC linker was obtained. The product is suitable for conjugation to primary antibodies.

What is claimed:

1. Process for production of 9-amino-anthracycline-derivatives at least comprising two oxazolidine moieties at the anthracycline, at least comprising the steps of:
   a) Suspending 9-amino-anthracycline according to the following Formula 1 in an aprotic solvent Formula 1 wherein R1 is selected from the group consisting of H, OH, OMe or F and R2 is selected from the group consisting of methyl, ethyl or propyl;
   b) Reacting formaldehyde and the two 1,2 amino-alcohol-moieties of the 9-amino- anthracycline to form an anthracycline according to the following Formula 2 comprising two oxazolidine moieties Formula 2

2. Process according to claim 1, wherein in step b) the molar ratio of formaldehyde to 9-amino-anthracycline of formula I (formaldehyde:anthracycline) is ≥0.1 and ≤10.

3. Process according to claim 1, wherein the concentration of the 9-amino-anthracycline of formula I in the solvent in step a) is ≥5 mM and ≤50 mM.

4. Process according to claim 1, wherein formaldehyde is used in form of paraformaldehyde and the molar ratio of formaldehyde to 9-amino-anthracycline of formula I (formaldehyde:anthracycline) is ≥1.0 and ≤2.0.

5. Process according to claim 1, wherein the aprotic solvent is HCCl3.

6. Process according to claim 1, wherein in an additional step c) anthracycline according to Formula 2 is reacted with linker molecules L to form a reaction product according to at least one of the following formula 3a-c

Formula 3a

Formula 3b

Formula 3c

7. Process according to claim 6, wherein the linker L is maleimidocaproyl-L-valine-L-citrulline-p-aminobenzoyl-carbamate 8. Process according to claim 6, wherein in an additional step d) the not linker-protected oxazolidine ring in formula 3a or 3b is hydrolyzed to yield the respective 1,2 amino-alcohol moiety according to the following formula 4a or 4b Formula 4a

Formula 4b

9. Process according to claim 6 or claim 8, wherein in an additional step e) an antibody is attached to the linker L of formulae 3a-c or attached to the linker L of formulae 4a-b to form an Antibody-Drug-Conjugate (ADC).

10. Anthracycline at least comprising two oxazolidine moieties at the anthracycline core according to the following Formula 2

Formula 2 wherein R1 is selected from the group consisting of H, OH, OMe or F and R2 is selected from the group consisting of methyl, ethyl or propyl.

11. Anthracyclines according to claim 10, wherein R2=methyl.

12. Antibody-drug-conjugate comprising an antibody, one or two linker-groups and a drug, characterized in that the drug is a 9-amino-anthracycline and the anthracycline comprises two oxazolidine moieties or one oxazolidine moiety and an 1,2 amino-alcohol-moiety at the anthracycline.

13. A pharmaceutical composition, at least comprising the Antibody-drug-conjugate according to claim 12 in a pharmaceutical acceptable carrier.

14. A method for the treatment of cancer in a subject, the method comprising administering to the subject the pharmaceutical composition according to claim 13.

* * * * *